US007332553B2

(12) United States Patent
Sellergren et al.

(10) Patent No.: US 7,332,553 B2
(45) Date of Patent: Feb. 19, 2008

(54) FUNCTIONAL MONOMERS FOR MOLECULAR RECOGNITION AND CATALYSIS

(75) Inventors: Börje Sellergren, Mainz (DE); Andrew Hall, Mainz (DE); Karine Chenon, St Maur des Fosses (FR); Rohini Karmalkar, Pune (IN)

(73) Assignee: MIP Technologies AB, Lund (SE)

( * ) Notice: Subject to any disclaimer, the term of this patent is extended or adjusted under 35 U.S.C. 154(b) by 0 days.

(21) Appl. No.: 11/599,452

(22) Filed: Nov. 15, 2006

(65) Prior Publication Data

US 2007/0106041 A1    May 10, 2007

Related U.S. Application Data

(62) Division of application No. 11/019,588, filed on Dec. 23, 2004, now Pat. No. 7,208,557, which is a division of application No. 10/169,799, filed as application No. PCT/SE01/000137 on Jan. 25, 2001, now Pat. No. 6,870,021.

(30) Foreign Application Priority Data

Jan. 28, 2000    (SE) ................................. 0000295
Jan. 28, 2000    (SE) ................................. 0000389

(51) Int. Cl.
    *C08F 291/00* (2006.01)
(52) U.S. Cl. ....................... 526/310; 526/199; 526/200; 526/208; 526/209; 526/211; 526/213; 526/214; 526/233; 526/234
(58) Field of Classification Search ................ 526/199, 526/200, 208, 209, 211, 213, 214, 233, 234, 526/310
    See application file for complete search history.

(56) References Cited

U.S. PATENT DOCUMENTS

| 2,868,796 A | 1/1959 | Cislak |
| 3,281,487 A | 10/1966 | Rowe, Jr. et al. |
| 5,310,648 A | 5/1994 | Arnold et al. |
| 5,401,825 A | 3/1995 | Kurz |
| 5,444,129 A | 8/1995 | Kurz |
| 5,786,428 A | 7/1998 | Arnold et al. |
| 5,858,296 A | 1/1999 | Domb |
| 6,063,637 A | 5/2000 | Arnold et al. |
| 6,217,901 B1 | 4/2001 | Perrott et al. |
| 6,310,110 B1 | 10/2001 | Markowitz et al. |

FOREIGN PATENT DOCUMENTS

| WO | WO 97/20639 | 6/1997 |
| WO | WO 98/07671 | 2/1998 |

OTHER PUBLICATIONS

Günther Wulff et al., "Polymerizable Amidines—Adhesion Mediators and Binding Sites for Molecular Imprinting", Advanced Materials, Research News, 1998, pp. 957 to 959, 10, No. 12,, Wiley-vch Verlag GmbH, D-69469 Weinheim, Germany.

Börje Sellergren, Department of Inorganic Chemistry and Analytical Chemistry, Johannes Gutenberg University, Mainz, J.J. Becherweg 24, 55099 Mainz, Germany, "Polymer and Template-Related Factors Influencing the Efficiency in Molecularly Imprinted Solid Phase Extractions," trends in analytical chemistry, 1999, pp. 164 to 174, vol. 18, No. 3, Elsevier Science B.V.

Helmut Ritter, et al., "Polymerizable Mesoions. 2.Radical Polymerization and 1,4 Dipolar Polycycloaddition of a 4-vinylphenyl modified mesoionic 4,6-dioxo-1,3-diazine;" Macromolecular Rapid Commun., 1995, pp. 407-415; 16(6), CAPLUS Accession No. 1995:613658, Document No. 123:10053 (Abstract).

R. Fuks, "N-Alkylation of Nitriles—I.A. General Synthesis of Substantiated Amidines," Tetrahedron, 1973, pp. 2147 to 2151, vol. 29 Pergamon Press 1973.

Masao Tomoi et al., "N-Alkylpentamethylphosphoramides: novel catalysts in two-phase reactions", Chem. Letters,1976, pp. 473 to 476, (5), CAPLUS Accession No. 1976:493728, Document No. 85:93728 (Abstract).

Benmaarouf-Khallaayoun, Z et al., "Hydroboration of Unsaturated Amines", XI. Regio-and Stereoselectivity of Boron Hydrides with Respect to N-phosphorylated propargylic amines, Journal of Organomet. Chem., 1986, pp. 283 to 293,306(3) CAPLUS Accession No. 1987:138532, (Abstract).

Bernard Corbel, et al., "N-Propargylphosphoramides—Nouveaux Reactifs De Synthese", Tetrahedron Letters, 1976, pp. 835 to 838, vol. 11, Pergamon Press, (Abstract).

Koichi Kondo, et al., "Synthesis of Functional Polymers Containing Carbodimide Groups", Technol. Rep. Osaka University, 1975, pp. 487-489, 25 (1254-1275), CAPLUS Accession No. 1976: 106103, Document No. 84:106103. (Abstract).

V.G. Sinyavskii et al., "Synthesis of 2-and 4-isocyanatostyrenes and Their Derivatives," Deposited Doc., VINITI 3283-78, 1978, p. 12, CAPLUS Accession No. 1980:76011, Document No. 92:76011. (Abstract).

Hiroyoshi Kamogawa et al., "Synthesis of Polymerizable Carbodimides Bearing a Terminal Vinyl Group," Bulletin of the Chemical Society of Japan, 1979, pp. 533 to 535, vol. 52, No. 2.

A. M. Shur et al., "Synthesis and Study of Some Monomers Containing Additional Chemically Active Groups", Sb. Nauch. Stratei, Kishinev, Gos. University, Estestv. Mat. Nauki, 1969, pp. 118-129, Kishinev. USSR, CAPLUS Accession No. 1971:111672,Document No. 74:111672. (Abstract).

(Continued)

*Primary Examiner*—Helen L Pezzuto
(74) *Attorney, Agent, or Firm*—Buchanan Ingersoll & Rooney PC

(57) ABSTRACT

The present invention refers to new classes of polymerisable monomers, to molecularly imprinted polymers obtainable by polymerisation of at least one of the monomers and a crosslinking monomer in the presence of a template molecule. The obtained polymers may be used for separation of enantiomers, diastereomers of the template molecule, and also for separation of the template molecule or template molecule analogues from structurally related compounds.

7 Claims, 2 Drawing Sheets

OTHER PUBLICATIONS

Margaret C. Ette et al., "1-3-Bis(m-nitrophenyl)urea: An Exceptionally Good Complexing Agent for Proton Acceptors," J. Am. Chem. Soc. Communications to the Editor, 1988, pp. 5896 to 5897, vol. 110, American Chemical Society.

Klaus Mosbach, "Molecular Imprinting", Trends in Biochemical Sciences, Jan. 1994, pp. 9 to 14, vol. 19, Elsevier Science Publishers (UK).

Börje Sellergren et al., "Highly Enantioselective and Substrate-Selective Polymers Obtained by Molecular Imprinting Utilizing Noncovalent Interactions. NMR and Chromatographic Studies on the Nature of Recognition," J. Am. Chemical Society, 1988, pp. 5853 to 5860, vol. 110, No. 17, American Chemical Society.

International Search Report dated May 30, 2001 and the International Preliminary Examination Report dated Apr. 18, 2002.

Masao Tomoi et al., "N-Alkylpentamethylphosphormaides: Novel Catalysts in Two-Phase Reactions", Chemistry Letters (1976), (5), 473-476.

FUNCTIONAL MONOMERS FOR MOLECULAR RECOGNITION AND CATALYSIS

This is a Divisional Application of U.S. patent application Ser. No. 11/019,588, filed Dec. 23, 2004, now U.S. Pat. No. 7,208,557, which is a Divisional Application of U.S. patent application Ser. No. 10/169,799, filed Nov. 25, 2002 (now U.S. Pat. No. 6,870,021) which is a 35 U.S.C. §371 filing of International Patent Application No. PCT/SE01/000137, filed Jan. 25, 2001.

TECHNICAL FIELD OF THE INVENTION

The present invention relates to new polymerisable functional monomers, to molecularly imprinted polymers obtainable by polymerisation of at least one of the monomers and a crosslinking monomer in the presence of a template molecule. The invention also relates to the use of said polymers.

BACKGROUND ART

In the fields of medical, dietary, environmental and chemical sciences there is an increasing need for the selective separation of specific substances in complex mixtures of related substances. The end goal can be the preparative isolation of a certain compound or compounds or measurements of their concentration. Molecularly imprinted polymers (MIPs) often exhibit a high selectivity towards their substrate in analogy with antibody-antigen complementarity. (1) The technique shows promise in chiral separations of, for example, amino acid derivatives, peptides, phosphonates, aminoalcohols and beta-blocking compounds, affinity chromatography of nucleotides and the DNA-bases, as well as substitutes for antibodies in immunoassays for commercial drugs. (2) Molecular imprinting (MI) consists of the following key steps (FIG. 1): (1) Functional monomers are allowed to interact reversibly with a template molecule in solution. (2) The hereby formed template assemblies are copolymerized with a crosslinking monomer resulting in a crosslinked network polymer. (3) The template is displaced and the materials can be used for selective molecular recognition of the corresponding compound. If these are crushed and sieved they can be packed in a chromatographic column and used for chromatographic separation of the template from structurally related analogues. Analytical as well as preparative applications are possible. Preparative applications can be separation of a compound from a complex mixture of structurally related compounds and isolation of the compound. This can be through an affinity chromatographic procedure where pH, ion strength or solvent gradients can be used in order to control the strength of interaction with the stationary phase. The separation can target enantiomers or diastereomers in a mixture of enantiomers or diastereomers of one or many compounds. Analytical applications can in addition to the above mentioned separations be: competitive binding assays, chemical sensors or selective sample enrichments. (3)

Currently the most widely applied technique to generate molecularly imprinted binding sites is represented by the noncovalent route. (4) This makes use of noncovalent self-assembly of the template with functional monomers prior to polymerisation, free radical polymerisation with a crosslinking monomer and then template extraction followed by rebinding by noncovalent interactions. Although the preparation of a MIP by this method is technically simple it relies on the success of stabilisation of the relatively weak interactions between the template and the functional monomers. Stable monomer-template assemblies will in turn lead to a larger concentration of high affinity binding sites in the resulting polymer. The materials can be synthesized in any standard equipped laboratory in a relatively short time and some of the MIPs exhibit binding affinities and selectivities in the order of those exhibited by antibodies towards their antigens. Most MIPs are synthesized by free radical polymerization of functional monounsaturated (vinylic, acrylic, methacrylic) monomers and an excess of crosslinking di- or tri-unsaturated (vinylic, acrylic, methacrylic) monomers resulting in porous organic network materials. These polymerisations have the advantage of being relatively robust allowing polymers to be prepared in high yield using different solvents (aqueous or organic) and at different temperatures. This is necessary in view of the varying solubilities of the template molecules.

The most successful noncovalent imprinting systems are based on commodity acrylic or methacrylic monomers, such as methacrylic acid (MAA), crosslinked with ethyleneglycol dimethacrylate (EDMA). Initially, derivatives of amino acid enantiomers were used as templates for the preparation of imprinted stationary phases for chiral separations (MICSPs) but this system has proven generally applicable to the imprinting of templates allowing hydrogen bonding or electrostatic interactions to develop with MAA. (5) The procedure applied to the imprinting with L-phenylalanine anilide (L-PA) is outlined in FIG. 1. In the first step, the template (L-PA), the functional monomer (MAA) and the crosslinking monomer (EDMA) are dissolved in a poorly hydrogen bonding solvent (diluent) of low to medium polarity. The free radical polymerisation is then initiated with an azo initiator, commonly azo-N,N'-bis-isobutyronitrile (AIBN) either by photochemical homolysis below room temperature or thermochemically at 60° C. or higher. In the final step, the resultant polymer is crushed by mortar and pestle or in a ball mill, extracted in a Soxhlet apparatus and sieved to a particle size suitable for chromatographic (25-38 μm) or batch (150-250 μm) applications. The polymers are then evaluated as stationary phases in chromatography by comparing the retention time or capacity factor (k') of the template with that of structurally related analogues.

A number of compound classes are only poorly recognized by polymers prepared using the present imprinting protocols. Furthermore the binding strength between the functional monomer and the template is often insufficient, leading to a low sample load capacity and significant non-specific binding. There is therefore a need for the development of new functional monomers binding more strongly to the template and allowing recognition of new compound classes. For instance monomers designed to bind carboxylic-, phosphoric- or phosphonic-acid templates are needed. A few examples are given here. One goal in the analytical applications is the development of imprinted polymers capable of strongly binding nucleotides and discriminating between the four bases. This may lead to new methods for sensitive detection of modified DNA bases and may thus find use in early cancer diagnosis. However, this requires development of new functional monomers capable of binding phosphate thereby increasing the organic solubility of the template. Moreover recognition of adducts of the four DNA bases formed upon exposure of DNA to oxidizing or alkylating agents is one important goal in the development of methods aiming at early diagnosis or prediction of cancer risks. However, this requires development of new functional monomers capable of binding purine and pyrimidine bases with high fidelity. In chiral separations and for analytical applications using imprinted polymers there is also a need for functional monomers capable of strongly binding compounds with weakly acidic hydrogens such as in alcohols, imides, sulfonamides, phosphonamides, ureas including important classes like carbohydrates, sulfonylureas, hydantoins, barbiturates, purine, pyrimidine and pteridine bases. If these were available, higher selectivities and capacities for the target compound or enantiomer could be expected. Weakly polar or nonpolar compounds are also an important group of targets that are difficult to bind with high selectivity. Among these are highly important and relevant analytes such as dioxines (tetrachlorodioxodibenzene, TCDB), polyaromatic hydrocarbons (PAHs), aldehydes, halogenated hydrocarbons and phosphonates (such as those found in nerve agents and insecticides).

This invention describes the synthesis and use of new classes of functional monomers for molecular imprinting. Two classes are based on the amidine-functional group and can be synthesized with various basicities, hydrophobicities and chiralities. Amidine functionalized monomers have been previously used in molecular imprinting in the form of derivatives of 4-vinylbenzamidine. (16) These are synthesized in several steps and can only be produced with a limited structural variation. Also no chiral amidine monomers have been reported for use in molecular imprinting. This invention introduces a new class of amidine based monomers, formamidines, that are accessible in high yield in only a few synthetic steps. The monomers are suited for imprinting of a variety of functional groups including carboxylic and phosphorous acids, alcohols, imides, sulfonamides, phosphonamides and ureas which can be achiral or chiral. Furthermore the synthetic route allows their properties such as pKa values and polarities to be easily tuned. The other class of amidine based monomers are chiral amidines that potentially will enhance the recognition of chiral substrates. This basic benzamidine unit has previously been used as chiral shift reagents in determination of optical purity by NMR. (17) Another class of functional monomers are vinyl-methacrylolyl- or acryoloyl-based alkyl or aryl diamines (4) which was previously used as a chiral shift reagent for diols. This monomer is designed to bind carbohydrates.

Other classes of polymerisable functional monomers of the present invention are receptor analogue monomers, urea based monomers, thiourea based monomers, purine or pteridine based monomers, acrylamido or methacrylamido pyridine monomers, aminovinylpyridine monomers, strong hydrogen bond accepting monomers that are unable to function as hydrogen bond donors, such as hexamethyl phosponamide based monomers, and strong hydrogen bond donating monomers that are unable to function as hydrogen bond acceptors, such as N,N'-disubstituted phenyl urea monomers, as defined below.

This invention describes the synthesis and use of new classes of functional monomers for molecular imprinting. They will be described below together with a number of non-restricting examples of their synthesis and use.

The invention will now be described in more detail giving a number of non-restricting examples:

SUMMARY OF THE INVENTION

Thus, the present invention relates to a polymerisable functional monomer, wherein said monomer is selected from at least one of the following:

a) a formamidine monomer;
b) a chiral amidine monomer;
c) a vinyl-methacrylolyl or acryoloylbased alkyl or aryl diamine;
d) a receptor analogue monomer of one of the following formulas

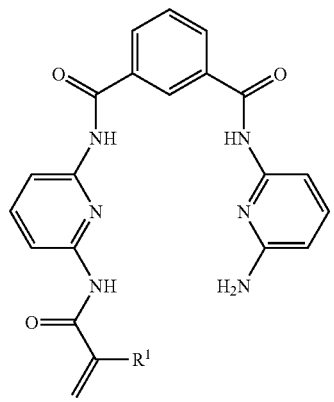

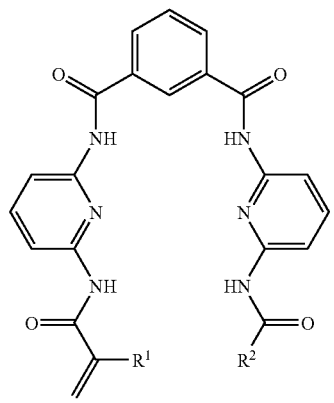

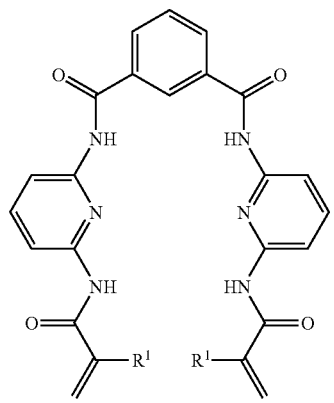

-continued

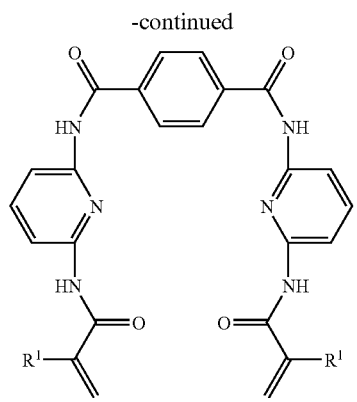

wherein each R¹ is independently selected from the group consisting of H and CH₃ and R² is independently selected from the group consisting of alkyl and aryl;

e) an urea monomer of the formula

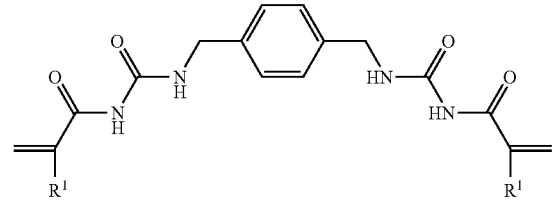

or

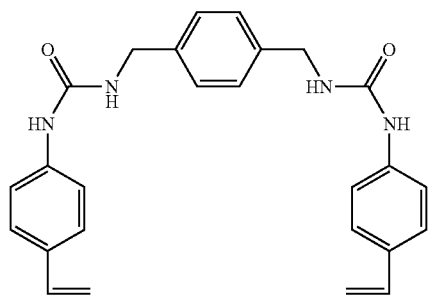

wherein each R¹ is independently selected from the group consisting of H and CH₃;

f) a thiourea monomer of the formula

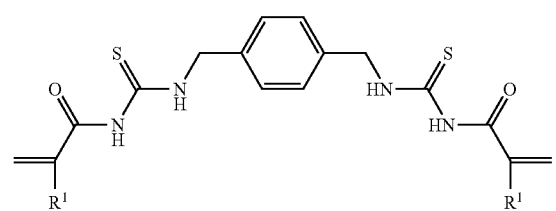

or

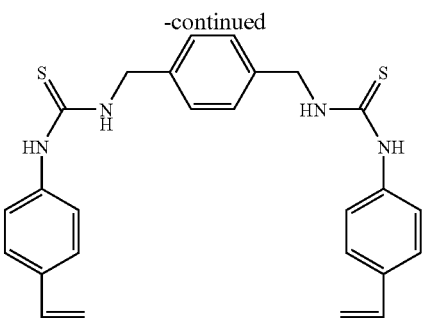

wherein each R¹ is independently selected from the group consisting of H and CH₃;

g) a purine or pteridine based monomer of one of the following formulas

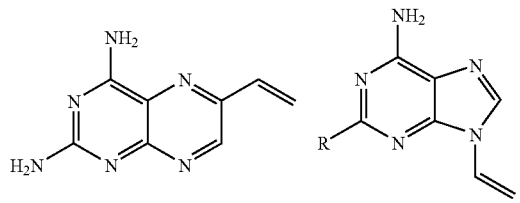

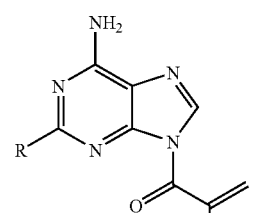

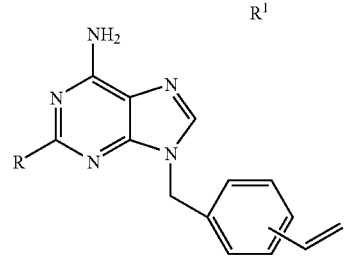

wherein each R is independently selected from the group consisting of H and NH₂ and R¹ is selected from the group consisting of H and CH₃;

h) an acrylamido or methacrylamido pyridine monomer of one of the following formulas

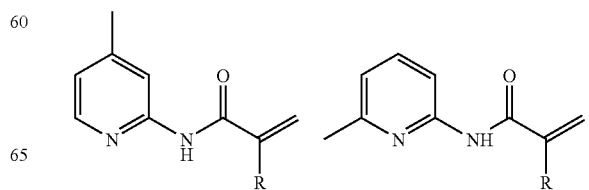

-continued

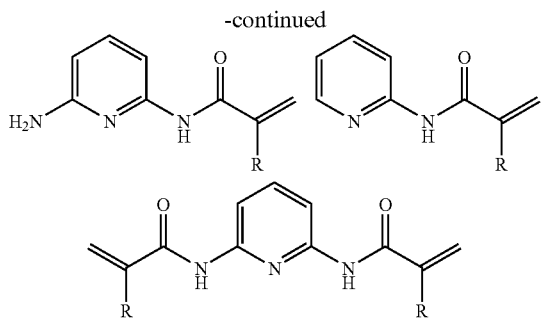

wherein each R is independently selected from the group consisting of H and CH$_3$;

i) an aminovinylpyridine monomer of one of the following formulas

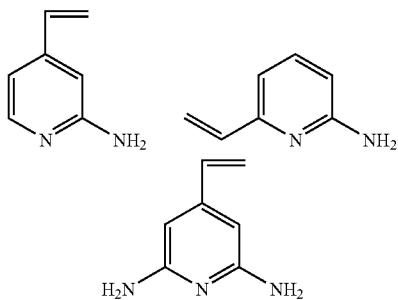

j) a strong hydrogen bond accepting monomer that is unable to function as a hydrogen bond donor, preferably a hexamethyl phosphonamide based monomer of the formula

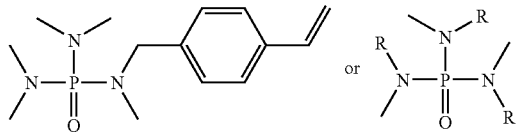

wherein each R is independently selected from the group consisting of styryl and vinylbenzyl;

k) a strong hydrogen bond donating monomer that is unable to function as a hydrogen bond acceptor, preferably a N,N'-disubstituted phenyl urea monomer of the formula

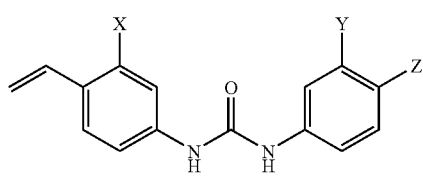

wherein X, Y and Z are independently selected from the group consisting of H, NO$_2$, CF$_3$ and halide.

The monomers a), j) and k) are particularly important aspects of the present invention.

The invention further relates to a polymer obtainable by polymerisation of at least one of the above monomers a)-k) and a crosslinking monomer in the presence of a template molecule.

Still further the invention relates to the use of a polymer according to the above for separation of enantiomers, diastereomers of the template molecule, and also for separation of the template molecule or template molecule analogues from structurally related compounds.

Yet further the invention relates to the use of said polymer for catalysing chemical reactions such as esterolysis, amidolysis, ester synthesis or amide synthesis.

PREFERRED EMBODIMENTS OF THE INVENTION

Figure 1:
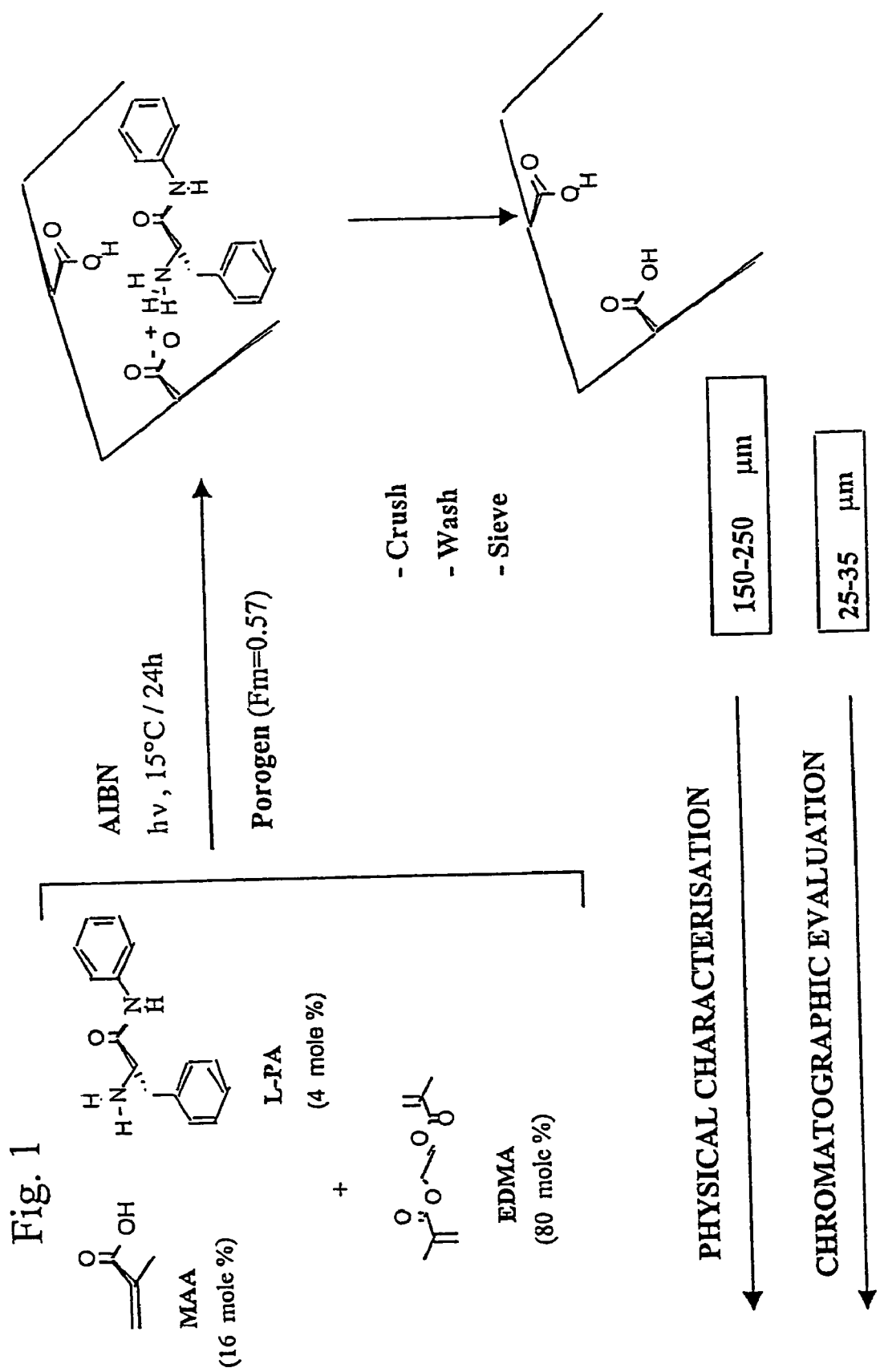
FIG. 1 illustrates molecular imprinting with L-phenylalanine anilide (L-PA).
Figure 2:
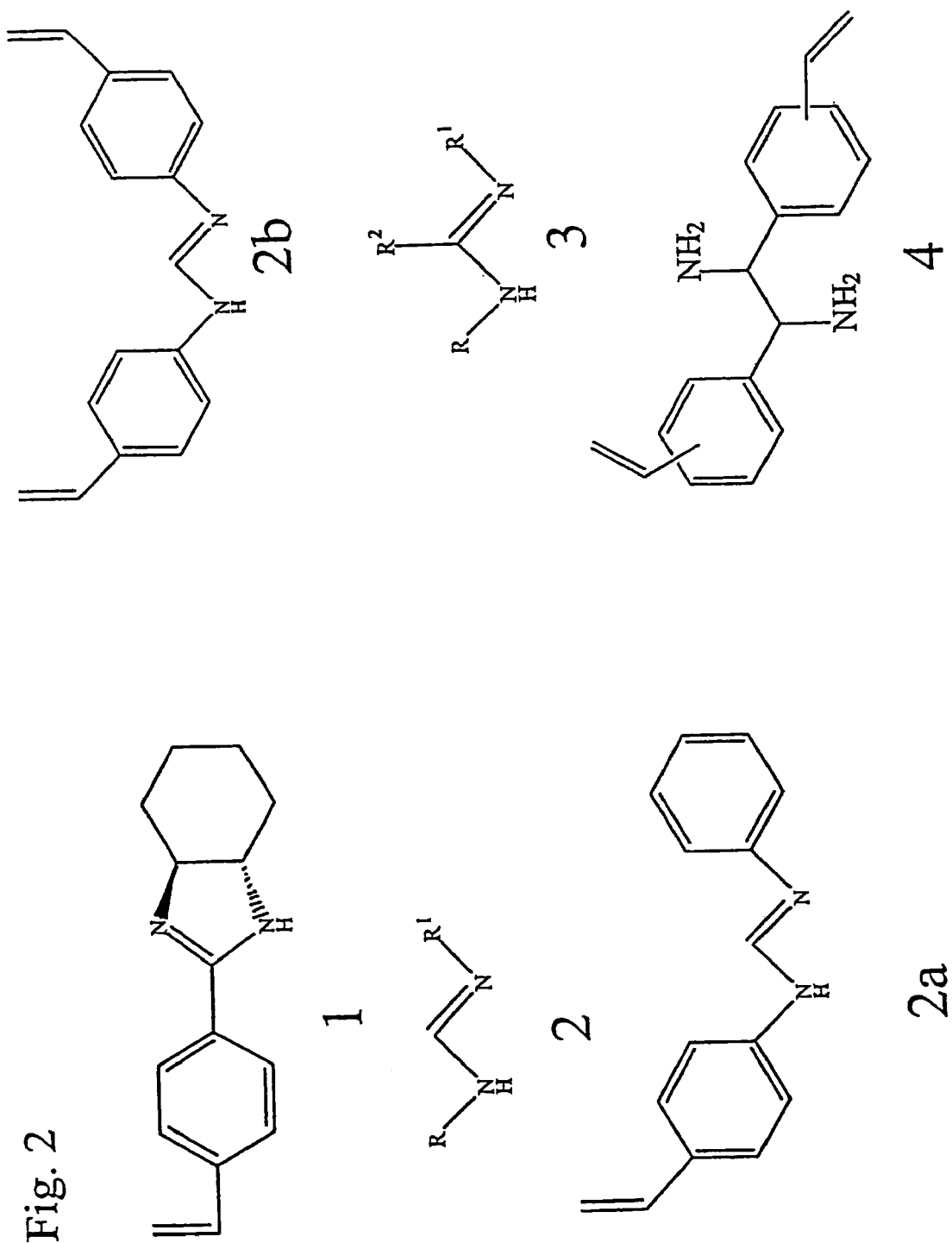
FIG. 2 illustrates several monomers according to the invention.

The invention will now be described in more detail with reference to a group of non-limiting examples.

According to one aspect of the present invention the amidine monomer is a formamidine.

In one aspect of the invention the amidine monomer is a cyclic amidine.

According to one aspect the cyclic amidine is formed from one enantiomer of cyclohexanediamine or substituted cyclohexanediamine.

According to another aspect the cyclic amidine is formed from ethylenediamine, 1,2-diphenyl-1,2-ethylenediamine or a 1,3-diamine.

The template molecule used in the polymerisation according to the present invention can be selected from the group consisting of a nucleotide or oligonucleotide, a polyelectrolyte such as a polysulfonic or polycarboxylic or mixed polysulfonic/polycarboxylic acid, a carboxylic acid, a phosphonic acid, a phosphoric or phosphinic acid, a sulfuric, sulfonic, sulfinic acid, an alcohol, an imide, a thiol, a ketone, an amide, a sulfonamide, a phosphonamide, a hydantoin, a barbiturate, an ether, a polyaromatic hydrocarbon, a phosphonate, an aldehyde.

EXAMPLES

1. Benzamidines and Chiral Amidines

Example 1

The chiral amidine monomer (1) is synthesized starting with a 4-bromobenzonitrile or another bromoarylnitrile, or a substituted bromoarylnitrile which is reacted to form the ethylimidate through a Pinner synthesis followed by reaction with a diamine that can be ethylenediamine, 1,2-diphenyl-1,2-ethylendiamine, (+) or (−) cyclohexyldiamine, a substituted chiral cyclohexyldiamine or a 1,3-diamine. After protection of the basic nitrogen a vinyl group is introduced by Pd-catalysed reaction between the protected amidine and vinyltributyltin (Stille coupling). After deprotection the amidine monomer is obtained.

Example 2

The amidine monomer is synthesized starting with 4-acetobenzonitrile or substituted 4-acetobenzonitrile which is reacted to form the ethylimidate through a Pinner synthesis followed by reaction with a diamine that can be ethylenediamine, 1,2-diphenyl-1,2-ethylendiamine, (+) or (−) cyclohexyldiamine, a substituted chiral cyclohexyldiamine or a 1,3-diamine. After protection of the basic nitrogen a Wittig reaction is performed by reacting the amidine with the corresponding methylylid. The final product is then obtained by deprotection of the amidine.

Example 3

Here we describe the synthesis of a range of amidine monomers, starting from 4-cyanostyrene, prepared using the classical Pinner synthesis. The preparation of the chiral amidine monomer (1) is described as an example of the general method.

Anhydrous ether is saturated with anhydrous HCl over the course of 1 hour. To this solution are added 4-cyanostyrene and anhydrous ethanol. Dry HCl is then bubbled through the solution for a further 3 hours, during which time a precipitate begins to form. The solution is left to stand for 18 hours. The large amount of precipitate forms is filtered off, washed with anhydrous ether and dried in vacuo over $P_2O_5$, yielding the intermediate imidate salt in 80% yield.

The intermediate imidate salt (1 equ.) is dissolved in anhydrous ethanol, with stirring, under an inert atmosphere. To this solution is added D-1,2-diaminocyclohexane (1 equ.). The resulting solution is stirred for 1 hour at 40° C. The solution is then heated to reflux for a further 2 hours and then allowed to cool. The cooled solution is poured onto aqueous 5% sodium hydrogen carbonate and the solution is then extracted with dichloromethane. The organic phases are combined, dried over magnesium sulphate and filtered. Removal of the solvent in vacuo yields the product, monomer (1), as a yellow solid in 70% yield.

A vast series of vinylbenzamidines may be prepared following the above procedure by substituting D-1,2-diaminocyclohexane for any desired amine or diamine.

2. Formamidines

N,N'-disubstituted formamidines, of the general formula shown below, are capable of both hydrogen bond donation and acceptance. The substituents R and $R^1$ may be varied so as to yield monomers with a wide range of basicity. A polymerisable moiety is carried either by R (2a) or by both substituents (cross-linking monomers 2b). Choosing R and R1 from aromatic based moieties, monomers with relatively low basicity are expected. However choosing them as aliphatic, for instance vinylbenzylamine, more basic monomers are expected with pKa values amounting to those typical for primary amidines (pKa>10). Choosing mixed aliphatic (R) and aromatic (R1), or R and R1 being aromatic with electron-donating/accepting substitutions, the basicity is expected to be easily tuned to match the particular application.

Two examples are given below, one for the preparation of monomers of type 2a and the second for monomers of type 2b.

The typical procedure for the preparation of monomers of type 2a is described below, using the synthesis of N-styryl-N'-phenyl formamidine as an example.

Example 4

The synthesis is achieved in three steps. The first step is the preparation of N,N'-diphenyl formamidine (by the reaction of aniline with triethyl orthoformate). This intermediate is then further reacted with triethyl orthoformate to produce ethyl N-phenylimidoformate. The final step is the reaction of ethyl phenylimidoformate with 4-aminostyrene to give the product.

Thus, a mixture of triethyl orthoformate (1 equ.) and aniline (2 equ.) is heated at reflux for 2 hours. The ethanol evolved during the reaction is then distilled through a fractionating column. The reaction mixture is then allowed to cool, whereupon it solidifies. Recrystallisation of the solid from toluene yields N,N'-diphenyl formamidine in 80% yield.

N,N'-diphenyl formamidine (1 equ.) and triethyl orthoformate (2 equ.) are mixed and a catalytic amount of dry aniline hydrochloride is then added. The mixture is heated and ethanol is seen to reflux within a few minutes. The mixture is heated at reflux for 1 hour and then the ethanol is distilled. Following the distillation, anhydrous potassium carbonate is added. The mixture is shaken and then allowed to stand for 2 hours. The reaction mixture is then distilled under reduced pressure. At 93 mmHg, excess triethyl orthoformate is collected at 83-85° C. The pressure is then reduced to 40 mmHg and ethyl N-phenylimdioformate is collected at 117° C. in 95% yield.

A mixture of ethyl N-phenylimdioformate (1 equ.) and freshly distilled 4-aminostyrene (1 equ.) are slowly heated, whereupon an exothermic reaction sets in. Care should be taken to control the temperature to below 60° C. After heating at 60° C. for 5 minutes, the reaction is cooled and left at −18° C. for 18 hours. The crude product is isolated and then recrystallised from ethanol to yield the product, N-styryl-N'-phenyl formamidine (2a) in 55% yield.

Example 5

The typical procedure for the preparation of monomers of type 2b is described below, using the synthesis of N,N'-distyryl formamidine as an example.

Thus, a mixture of triethyl orthoformate (1 equ.) and glacial acetic acid (1 equ.) is heated at reflux for 30 minutes. Freshly distilled 4-aminostyrene (2 equ.) is added dropwise to the refluxing mixture. The reaction mixture is heated at reflux for 45 minutes. The apparatus is then set for distillation and the reaction mixture heated such that volatile material is distilled. After distillation of volatile material has ceased, the reaction mixture is allowed to cool to room temperature and is then evacuated for 18 hours (<1 mbar). The crude solid product is shaken with aqueous sodium carbonate and extracted with diethyl ether. The combined ethereal extracts are dried over magnesium sulphate and then evaporated to dryness.

Recrystallisation from petroleum ether 60-80 affords the product (2b) as white crystals.

3. Further Amidines

A wide range of monomeric amidines may also be prepared by the method of Fuks. (18) This procedure has previously been used to prepare acrylamidines. However, these compounds polymerise not only via addition polymerisation of the vinylic group, but also via a polyaddition reaction between the amidine and the vinylic group. Thus, acrylamidines are of little use in the preparation of MIPs.

However, the method is general for the preparation of amidines and polymerisable molecules can indeed be obtained.

Here, we describe the preparation of monomers (3), where any or all of the groups R, $R^1$ and $R^2$ may carry a polymerisable function. The typical procedure is described below, using the synthesis of N-isopropyl-N'-vinylbenzyl-acetamidine (R=$^i$Pr, $R^1$=vinylbenzyl and $R^2$=$CH_3$) as an example.

Example 6

Thus, a suspension containing iron (III) chloride (1 equ.) in a large excess of isopropyl chloride is mixed with acetonitrile (1 equ.) at 0° C. The suspension is stirred for 3 hours. The excess isopropyl chloride is removed in vacuo to leave a solid residue. This residue is taken up in dichloromethane and a solution of vinylbenzyl amine (0.95 equ.) in dichloromethane is added dropwise to the suspension. The mixture is stirred for two hours at room temperature, after which time the solvent is removed in vacuo and the residue is taken up in water. The mixture is cooled to 0° C. and 30% aqueous sodium hydroxide (4.5 equ.) is added. This mixture is extracted with four times with diethyl ether. The ethereal extracts are combined, dried over magnesium sulphate, filtered and then reduced in vacuo. The solid is recrystallised from petroleum ether 40-60 to yield the product (3) in 60% yield.

Example 7

The polymer is synthesized by free radical polymerisation of a mixture of any of the amidine monomers prepared as described in Examples 1-6, and a crosslinking monomer, that can be for example ethyleneglycoldimethacrylate, divinylbenzene or trimethylolpropanetrimethacrylate, in presence of a solvent and a template and an initiator, that can be azobisisobutyronitrile. A third monomer, that can be methacrylic acid or fluoromethylacrylic acid can also be added. The template can be a nucleotide or oligonucleotide, a polyelectrolyte such as a polysulfonic or polycarboxylic or mixed polysulfonic/polycarboxylic acid, a peptide, a protein, a carboxylic acid, a phosphonic acid, a phosphoric or phosphinic acid, a sulfuric, sulfonic, sulfinic acid, or compounds with weakly acidic hydrogens such as alcohols, imides, sulfonamides, phosphonamides, ureas including important classes like carbohydrates, sulfonylureas, hydantoins, barbiturates, purine, pyrimidine and pteridine bases. Furthermore ketones may be suitable templates. The template can also be a transition state analogue for a chemical reaction. In the case where the template has one or more chiral centres the template may be one enantiomer or diastereomer of the template isomers. After polymerisation the polymer is freed from the template by a washing procedure.

Example 8

The polymer prepared according to Example 7 can be used for separation of enantiomers, diastereomers of the template or for separation of the template or template analogues from structurally related compounds. This can be done by chromatography, capillary electrophoresis, capillary electrochromatography, batch modes or membrane modes. The polymer can further be used for catalysing chemical reactions such as esterolysis, amidolysis, ester synthesis or amide synthesis.

4. Receptor Analogue Monomers

Molecules such as (I) have been identified as recognition elements for a variety of substrates, including barbiturates and dicarboxylic acids. (8) In molecular imprinting an important advantage is gained in using polymerisable versions of these kind of receptors. Many important biomolecules, i.e. peptides, proteins, cofactors and vitamins, contain discrete diacids as structural features that may be in the form of the amino acids aspartic and glutamic acid. With monomers available for selective complexation of these substructures other monomers can be added in the imprinting step to target other parts of the target molecules. One example of this principle is seen for the recognition of the dihydrofolate-reductase inhibitor methotrexate (A). Here we describe the synthesis of analogous molecules containing polymerisable functions (II a/b/c). The synthesis proceeds through the intermediate (IV), which is central to all the monomers described.

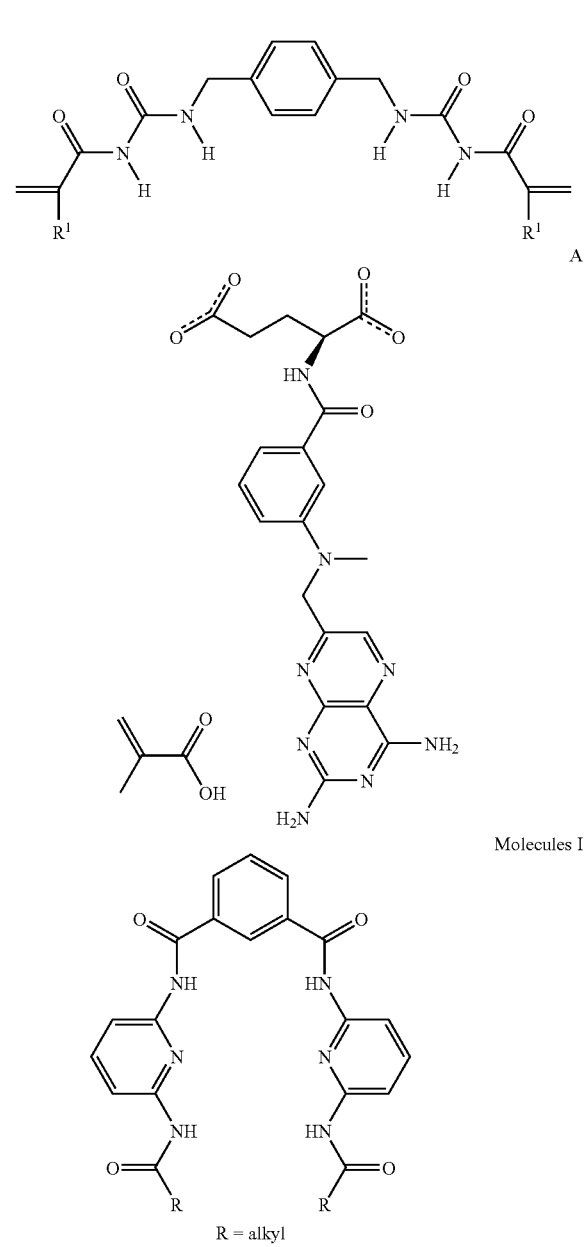

Molecules I

-continued

Intermediate IV

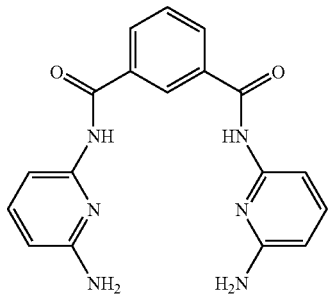

A further set of monomers (IIIa/b/c) may be prepared by using a terephthaloyl-spacer unit in place of the isophthaloyl-spacer shown above. These monomers are prepared in the same manner as described below for IIa/b/c (the structure of a type IIIc monomer is shown below).

Example 9

Intermediate (IV)

To a solution of 2,6-diaminopyridine (10 equ.) and triethylamine (2 equ.) in THF is added dropwise a THF solution of isophthaloyl dichloride (1 equ.) at room temperature under an inert atmosphere. The reaction mixture is stirred for 3 hours, after which time the solvent is removed in vacuo. The residue is stirred with water and the resulting precipitate filtered and washed well with more water (to remove excess diamine and triethylamine hydrochloride). The product is initially purified via alumina chromatography (DCM/THF as eluant) and finally by recrystallisation from THF/heptane. This yields the product (intermediate 10) as a faintly yellow crystalline solid in 79% yield.

The monomers listed are all products from the reaction of compound (IV) with either one equivalent of acid chloride (mono-functional monomers IIa), the further reaction of type IIa monomers with a different acid chloride (mono-functional monomers IIb) or two equivalents of the desired acid chloride(cross-linking monomers IIc). The methods are described below.

Monomers IIa

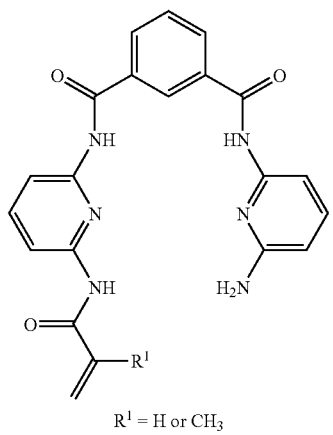

$R^1$ = H or CH$_3$

Monomers IIb

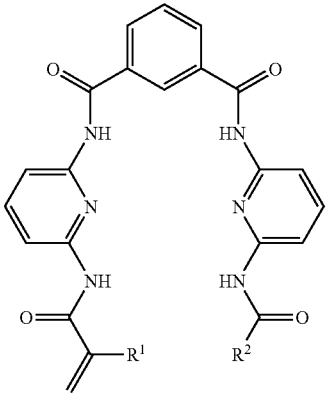

$R^1$ = H or CH$_3$
$R^2$ = alkyl or aryl

Monomers IIc

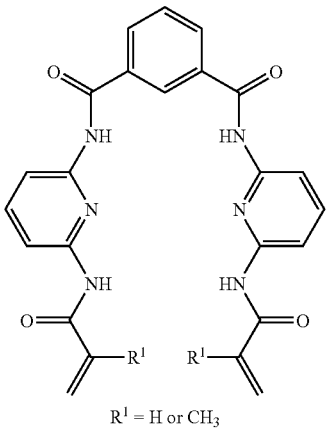

$R^1$ = H or CH$_3$

Monomers IIIc

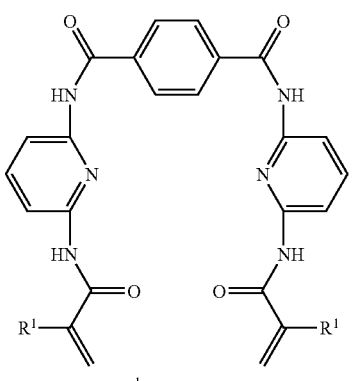

$R^1$ = H or CH$_3$

Example 10

Monofunctional Monomers IIa

Compound (IV) (1 equ.) and triethylamine (1.5 equ.) are dissolved in THF. To this solution is added dropwise a THF solution of acryloyl- or methacryloyl-chloride (1.5 equ) at room temperature under an inert atmosphere. The reaction mixture is stirred for 2 hours, after which time the precipitate is removed by filtration and the filtrate reduced to dryness in vacuo. The residue is washed with 0.05M aqueous NaOH, followed by water. The product is dispersed in 0.05M HCl and any insoluble material is removed by filtration. The solution is neutralised with NaHCO$_3$ and then extracted with chloroform. The chloroform extracts are dried (magnesium sulphate), filtered and reduced to dryness in vacuo. The solid residue is subjected to silica chromatography and the desired product is obtained in 30% yield.

Example 11

Monofunctional Monomers IIb

Compounds IIb are prepared via the reaction of compounds IIa with the desired acid chloride, in essentially the same manner described for the preparation of compounds IIa. The reaction mixture is stirred for 4 hours, after which time the precipitate is removed by filtration and the filtrate reduced to dryness in vacuo. The residue is washed successively with aqueous 0.05M NaOH, aqueous 0.05M HCl and water. Recrystallisation from THF/hexane gives the products in 20% yield.

Example 12

Crosslinking Monomers IIc

Compounds (IV) (1 equ.) and triethylamine (6 equ.) are dissolved in THF. To this solution is added dropwise a THF solution of acryloyl- or methacryloyl-chloride (4 equ.) at room temperature under an inert atmosphere. The reaction mixture is stirred for 4 hours, after which time the precipitate is removed by filtration and the filtrate reduced to dryness in vacuo. The residue is washed successively with aqueous 0.05M NaOH, aqueous 0.05M HCl and water. Recrystallisation from THF/hexane gives the products in 70% yield.

Molecules such as (V) have been identified as recognition elements for dicarboxylate salts, e.g. glutarates. The incorporation of such molecules into molecularly imprinted polymers could prove a powerful tool in the selective uptake of many biological substrates and pharmaceuticals, e.g. the anti-cancer drug methotrexate (which contains a glutamic acid residue). Here we describe the synthesis of analogous molecules containing polymerisable functions (ureas VIa/b/c and thioureas VIIIa/b/c).

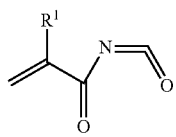

Molecules V

X = O or S
R = alkyl

Monomers VI

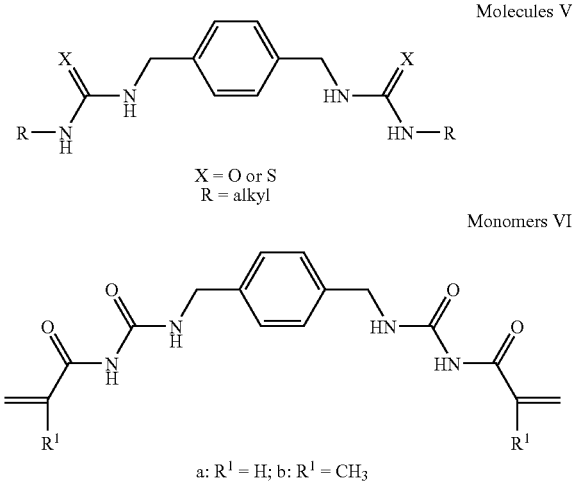

a: R$^1$ = H; b: R$^1$ = CH$_3$

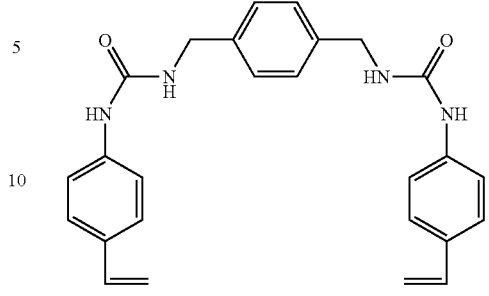

Monomer VIc

These syntheses involve the preparation of the functional isocyanates (VIIa/b/c). Isocyanates VIIa/b may be prepared by the method of Lieser. (9) This involves the reaction of the appropriate acid chloride with sodium cyanate in ethereal solution. Isocyanate VIIc may be prepared by the method of Iwakura et al. (10) This involves the reaction of 4-vinylbenzoyl chloride with sodium azide, followed by a Curtius rearrangement of the formed 4-vinylbenzazide to yield isocyanate VIIc.

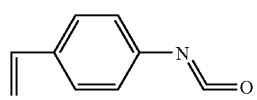

Isocyanates VIIa/b        Isocyanates VIIc a : R$^1$ = H; b : R$^1$ = CH$_3$

Example 13

Monomers VIa/b/c

These molecules are prepared via the reaction of isocyanates VIIa/b/c, respectively, with 1,4-xylylene diamine. Thus, a dilute solution of 1,4-xylylene diamine (1 equ.) in diethyl ether is added dropwise to a cooled ethereal solution of the desired isocyanate (1 equ.). The precipitate is filtered, washed well with diethyl ether and recrystallised from ethanol to give the desired product in 70% yield.

Extensions to the above schemes involve the reaction of isocyanates VIIa/b/c with any desired amine (or diamine), thus forming a vast library of polymerisable ureas for use in molecularly imprinted polymers.

There also exist other methods by which polymerisable ureas may be prepared, in which the preparation of isocyanates VIIa/b/c is precluded.

One example is the method of Johnson et al. (1392-1393 (1959)), which proceeds via the dehydrohalogenation of N-propionyl-N'-aryl ureas. These ureas are formed via the reaction of propionyl isocyanate with the appropriate aryl amine. The isocyanate, prepared from allyl amine and N-bromosuccinimide, need not be isolated and the ureas may be formed in the same flask as the preparation of the isocyanate was effected.

A further example is the reaction of activated esters, e.g. alk-1-en-2-yl esters, with the sodium salts of N-phenyl ureas in THF. (11) Here, there is no requirement for the preparation of isocyanates at all.

Syntheses of thioureas involve the preparation of the functional isocyanates (IXa/b/c), which may be prepared by the methods described in the following articles:

(i) IXa/b —U.S. Pat. No. 2,327,985 (1940) (to Du Pont de Nemours & Co.)
(ii) IXc—Overberger & Friedman, *J. Org. Chem.*, 30, 1926-1929 (1965)

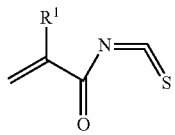
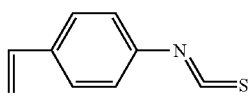

Isocyanates IXa/b    Isocyanates IXc a : R¹ = H; b : R¹ = CH₃

Example 14

Monomers VIIIa/b/c

Thiourea monomers VIIIa/b/c, the sulphur analogues of the ureas described above, may be prepared in a similar manner from the desired isothiocyanate and 1,4-xylylene diamine.

Example 15

Further Thioureide Monomers

Again in analogy to the compounds described above, extensions to the above schemes involve the reaction of isothiocyanates IXa/b/c with any desired amine (or diamine), thus forming a vast library of polymerisable thioureas for use in molecularly imprinted polymers.

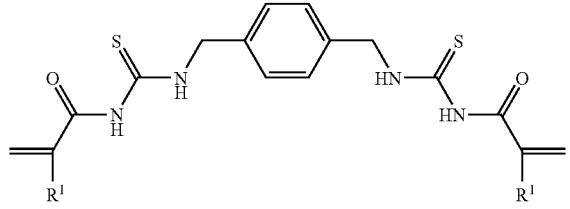

Monomers VIII a: R¹ = H; b: R¹ = CH

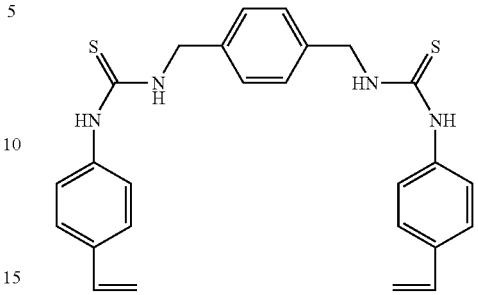

Monomer VIIIc

5. Purine and Pteridine Based Monomers

The hydrogen-bonding capabilities of purinic molecules are well established, e.g. their role in the structure of DNA. Adenines have previously been used as templates in the fabrication of MIPs using acidic monomers as recognition elements. (6) As a "flip-side" to this, polymerisable purinic molecules, will provide recognition elements for the molecular imprinting of acidic compounds. Furthermore strong complexes between adenine and a large number of important target molecules have been observed. Examples of these are complexes between adenine or derivatives thereof and riboflavin or analogues of riboflavin (B) and with imidic functions such as those found in hydantoins (C) or barbiturates. With pteridine-based functional monomers additional hydrogen bond donor/acceptor arrangements are available. These type of monomers, as well as the purine based monomers, offer multiple sites (faces) for interaction with a given target. The target will thus select the interaction site providing the maximum stability of the complex. Thus one or a few functional monomers can be used to target a vast array of molecular targets.

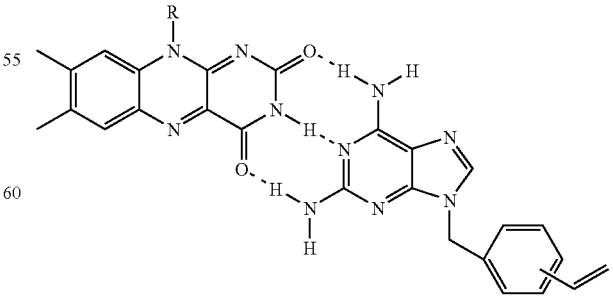

B

-continued

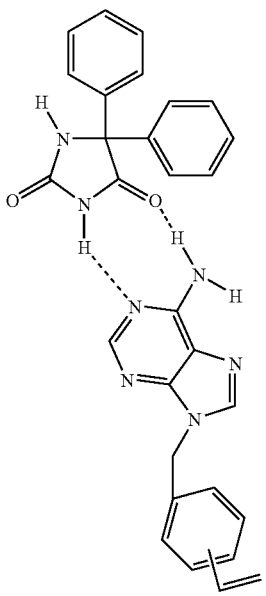

Example 16

9-vinylbenzyl-aminopurines (Xa/b)

6-amino-9-vinylbenzylpurine(9-vinylbenzyladenine) (Xa) and 2,6-diamino-9-vinylbenzylpurine (Xb) are synthesised as shown below via the alkylation of the parent purine with vinylbenzyl chloride (mixture of 3- and 4-isomers).

Monomers X

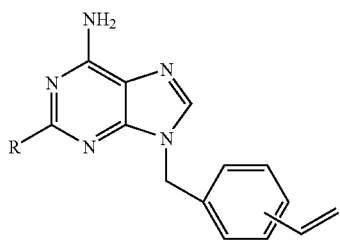

a : R = H; b : R = NH$_2$

A mixture of adenine (2.70 g, 20 mmol), 9-vinylbenzyl chloride (a mixture of 3- and 4-isomers) (3.36 g, 22 mmol) and potassium carbonate (5.52 g, 40 mmol) in dimethylformamide (150 cm$^3$) is stirred at room temperature under nitrogen for seven days. The resultant mixture is filtered and the filtrate was evaporated to dryness in vacuo (temperature below 40° C.) to give a yellow solid which is washed well with water.

The solid is dissolved in chloroform and the solution washed with 1M aqueous hydrochloric acid. The combined aqueous phases are extracted with chloroform and then basified by the slow addition of 5M aqueous sodium hydroxide with cooling (ice-water bath). The aqueous phase is then extracted with chloroform. The combined chloroform extracts are dried over magnesium sulphate, filtered and evaporated to give a white solid.

The solid is purified by column chromatography (9:1 chloroform:methanol as eluant) to yield spectroscopically pure 6-amino-9-vinylbenzylpurine (Xa) in 30% yield.

Example 17

9-vinyl-aminopurines (XIa/b)

6-amino-9-vinylpurine(9-vinyladenine) (XIa) and 2,6-diamino-9-vinylpurine (XIb) are synthesised as shown below. The first step involves the alkylation of the parent purine with (2-bromoethyl)methyl ether; this is followed by the elimination of methanol by the action of potassium t-butoxide.

Monomers XI

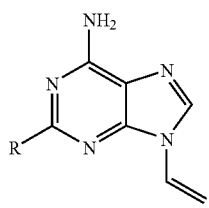

a : R = H; b : R = NH$_2$

Example 18

9-acryloyl- and 9-methacryloyl-aminopurines (XII)

These acryloyl and methacryloyl aminopurine derivatives are synthesised via the reaction of the appropriate aminopurine with acryloyl chloride and methacryloyl chloride respectively, as shown below.

Monomers XII

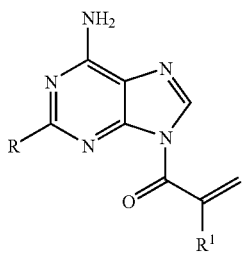

a$^1$ : R = H, R$^1$ = H; a$^2$ : R = H, R$^1$ = CH$_3$ b$^1$ : R = NH$_2$, R$^1$ = H; b$^2$ : R = NH$_2$, R$^1$ = CH$_3$

Example 19

Vinylpteridine Monomer (XIII)

An interesting extension of the above systems is the preparation and use of a pteridine-based monomer. Such an example is 2,4-diamino-6-vinylpteridine (XIII). This molecule is synthesised in five synthetic steps, from—chloropyruvaldoxime, in 15% yield following the method of Taylor & Kobayashi (*J. Org. Chem.*, 38, 2187-2821 (1973)).

Monomer XIII

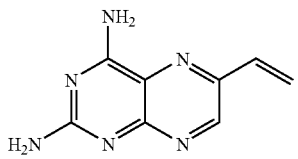

6. Aminopyridine Based Monomers

Pyridine moieties have been used in the fabrication of MIPs with the aim of providing sites for the recognition of acidic moieties in template molecules. Most commonly used have been the commercially available 2- and 4-vinylpyridines respectively. Acrylamido-(12) and methacrylamido-(13) pyridines have previously been synthesised and the latter have been incorporated into MIPs. Here, we describe a new class of aminopyridine monomers with tunable basicity and polarity. These have been successfully used in the synthesis of imprinted polymers showing high selectivity for molecules containing acidic functional groups. Methyl groups in the ring are used to tune polarity and basicity.

Acrylamido- and methacrylamido-pyridines (XIV-XVIII)

The monomers XIV to XVIII are all synthesised in essentially the same manner via the reaction of the appropriate 2-aminopyridine derivative with the desired acid chloride in dichloromethane, with triethylamine as base. The products are obtained in 50-70% yield following purification by silica gel chromatography. The preparation of monomer XVb is described as an example of the general procedure.

Example 20

A solution of 2-amino-6-methyl pyridine (1 equ.) and triethylamine (1.1 equ.) in dichloromethane is cooled to 0° C. Methacryloyl chloride (1 equ.) is added dropwise to the cooled solution and the solution is allowed to stir for 1 hour, the temperature being allowed to rise to room temperature. Water is then added and the resultant solution stirred for a further 30 minutes. After this time, the organic layer is separated from the aqueous phase, which is washed three times with dichloromethane. The combined organic phases are dried over magnesium sulphate, filtered and reduced to dryness in vacuo. The solid residue is then purified by silica gel chromatography to give the product, XVb, in 60% yield.

Monomers XIV

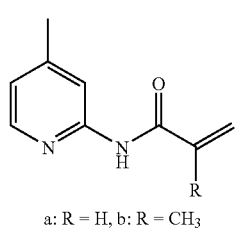

a: R = H, b: R = $CH_3$

Monomers XV

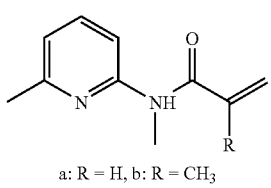

a: R = H, b: R = $CH_3$

-continued

Monomers XVI

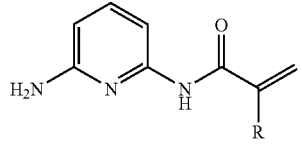

a: R = H, b: R = $CH_3$

Monomers XVII

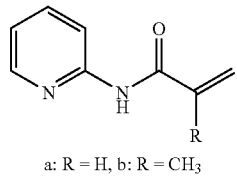

a: R = H, b: R = $CH_3$

Monomers XVIII

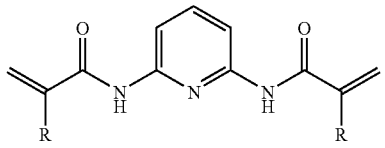

a: R = H, b: R = $CH_3$

Aminovinylpyridines (XIX-XXI)

The monomers XIX to XXI are prepared from the corresponding methyl substituted aminopyridines in two steps. The first is the alkylation of the methyl group via its reaction with n-butyl lithium and (chloromethyl)methyl ether. The resulting compound is then treated with potassium t-butoxide in the second step to give the vinyl-functionalised aminopyridine via the removal of methanol. The preparation of monomer XIX is described as an example of the general procedure.

Monomer XIX

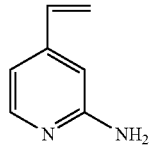

Monomer XX

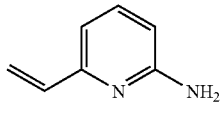

Monomer XXI

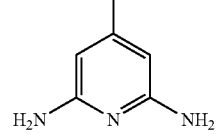

Example 21

Synthesis of Monomer XIX

A solution of n-butyl lithium (1 equ.) in hexane and tetrahydrofuran is cooled to 0° C., under an inert atmosphere. To the cooled solution is added dropwise a solution of 2-amino-4-methyl pyridine in tetrahydrofuran. The temperature is maintained at 0° C. and the solution stirred for a further 30 minutes once the addition is complete. A solution of chloromethyl)methyl ether (1.1 equ.) in tetrahydrofuran is then added dropwise to the reaction solution, with the temperature maintained at 0° C. After the addition is complete, the solution is stirred for a further 30 minutes, after which time the reaction is quenched by the addition of water. The reaction mixture is then partitioned between saturated aqueous sodium hydrogen carbonate and diethyl ether. The ethereal layer is separated and the aqueous phase is washed three times with diethyl ether. The ethereal extracts are combined, dried over magnesium sulphate, filtered and reduced to dryness in vacuo. The residue is then purified by silica gel chromatography to yield the intermediate ether in 70% yield. The intermediate ether (1 equ.) is dissolved in tetrahydrofuran and the solution is cooled to −78° C. under an inert atmosphere. To this solution is added a solution of potassium t-butoxide (2 equ.) in tetrahydrofuran. The reaction is stirred for 90 minutes at −78° C., before the temperature is allowed to rise to room temperature, whence it is stirred for a further 30 minutes. The reaction is then quenched by the addition of water. The reaction mixture is then extracted three times with diethyl ether. The ethereal extracts are combined, dried over magnesium sulphate and reduced to dryness in vacuo. The residue is purified by silica gel chromatography to yield the product XIX in 40% overall yield.

7. Strong Hydrogen Bond Acceptors

An example of molecules which can perform only as strong hydrogen bond acceptors is hexamethyl phosphonamide (HMPA). (14) Here we describe the synthesis of polymerisable analogues of HMPA, bearing either one

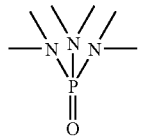

Hexamethylphosphonamid (HMPA)

polymerisable function (monomers XXII) or three polymerisable functions (cross-linking monomer XXIII). This new class of functional monomers is of great importance in molecular imprinting for the strong solubilization of poorly soluble templates in organic solvents. Its general use as a polymerisable solubilizing agent will allow the extension of molecular imprinting to other new compound classes.

Example 22

Functional Monomer XXI

This monomer is obtained via the reaction of the sodium salt of pentamethylphosphonamide with vinylbenzylchloride.

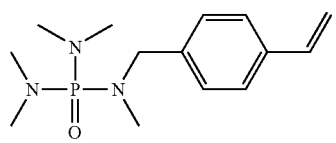

Monomer XXII

Thus, the sodium salt of pentamethylphosphonamide (1 equ.) and vinylbenzylchloride (1 equ.) are reacted together in toluene at 0° C. The pure monomer XXII is obtained in 60% yield following distillation under reduced pressure.

Example 23

Functional Monomers XXIIIa/b

These monomers are synthesised in two steps. The preparation of these tri-functional monomers is explained below, using the preparation of N,N',N''-tri(vinylbenzyl)-N,N',N''-tri(methyl)phosphonamide (XXIIIb), as the example.

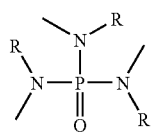

Monomers XXIII a: R = styryl; b: R = vinylbenzyl

To a stirred, cooled, chloroform solution of phosphoryl chloride (1 equ.) is added dropwise pyridine (3 equ.). The temperature of the solution is maintained at 0° C. during the course of the addition. The solution is transferred to a dropping funnel and added dropwise to a stirred, cooled (0° C.) chloroform solution of vinylbenzylamine (6 equ.). Once the addition is complete, the reaction mixture is refluxed for 2 hours to ensure complete reaction and then allowed to cool. Any insoluble material that appears on cooling is filtered and washed with chloroform. The combined chloroform portions are then reduced to dryness in vacuo. The residue is washed with dilute aqueous HCl and then with water. The solid was recrystallised from ethanol to yield N,N',N''-tri(vinylbenzyl)phosphonamide in 60% yield. N,N',N''-tri(vinylbenzyl)phosphonamide is converted to the monomer XXIIIb by reaction with methyl iodide and the pure product is obtained in 50% overall yield, after distillation under reduced pressure.

8. Strong Hydrogen Bond Donors

N,N'-disubstituted phenyl ureas, where (at least) one of the phenyl substituents bears an electron withdrawing group in the meta-position, are examples of compounds capable of hydrogen bond donation only. (15) These have proved to be exceptionally good complexing agents for hydrogen bond acceptors such as ethers, ketones and phosphonates. Monomeric versions of analogous structures to be used in molecular imprinting offers a new way into materials with good recognition properties for highly interesting targets such as dioxines (D), nerve agents, PAHs, ketones, aldehydes etc. Polymerisable examples of such compounds are illustrated below.

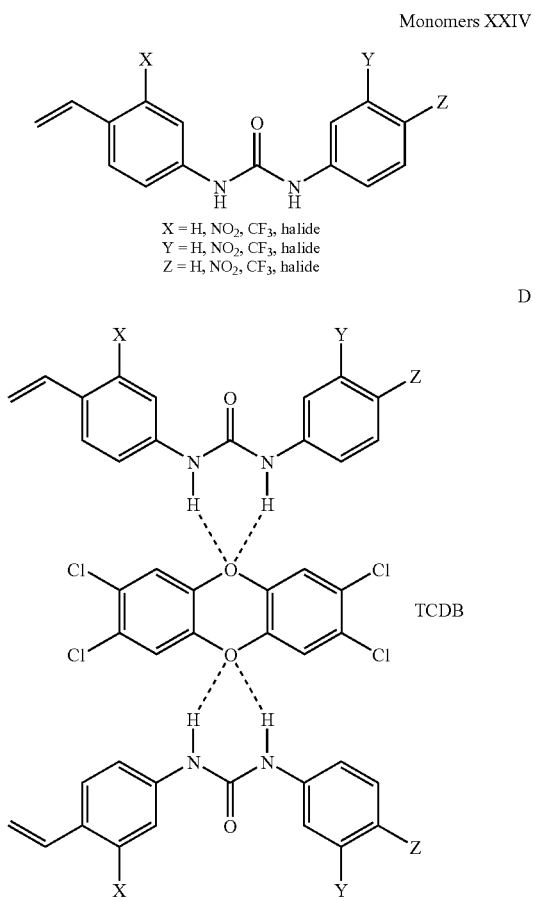

Monomers XXIV

X = H, NO$_2$, CF$_3$, halide
Y = H, NO$_2$, CF$_3$, halide
Z = H, NO$_2$, CF$_3$, halide

TCDB

Example 24

Synthesis of Monomers XXIV

These compounds may be prepared by the reaction of 4-aminostyrenes and the appropriate m-substituted phenyl isocyanate. The typical procedure is described below, using the synthesis of N-styryl-N'-(m-nitrophenyl)urea. Thus, 3-nitrophenyl isocyanate (1 equ.) and triethylamine (1 equ.) are dissolved in dimethylformamide. To the stirred solution is added 4-aminostyrene (1 equ.). The resultant solution is stirred overnight at room temperature. The red solution is then poured onto a mixture of crushed ice/water, causing the product to precipitate. The yellow precipitate is filtered off and washed well with water. The washed residue is purified by silica gel chromatography to give the product in 70% yield.

Such monomeric aromatic ureas may also be prepared by the reaction of vinylphenyl isocyanate (described previously—isocyanate VIIb) with substituted aromatic amines. The procedure is essentially the same as that described in the above paragraph.

Example 25

The polymer is synthesized by free radical polymerisation of a mixture of any of the monomers prepared as described in Examples 1 to 24 and a crosslinking monomer, that can be ethyleneglycoldimethacrylate, divinylbenzene or trimethylolpropanetrimethacrylate, in presence of a solvent and a template and an initiator, that can be azobisisobutyronitrile. A third monomer, that can be methacrylic acid or fluoromethylacrylic acid can also be added. The template can be a nucleotide or oligonucleotide, a polyelectrolyte such as a polysulfonic or polycarboxylic or mixed polysulfonic/polycarboxylicacid, a peptide, a protein, a carboxylic acid, a phosphonic acid, a phosphoric or phosphinic acid, a sulfuric, sulfonic, sulfinic acid, or compounds with weakly acidic hydrogens such as alcohols, imides, sulfonamides, phosphonamides, ureas including important classes like carbohydrates, sulfonylureas, hydantoins, barbiturates, purine, pyrimidine and pteridine bases. Furthermore may ketones and aldehydes be suitable templates. The template can also be a transition state analogue for a chemical reaction. In the case where the template has one or more chiral centres the template may be one enantiomer or diastereomer of the template isomers. The template can further be a hydantoin (e.g. diphenylhydantoin), flavin (e.g. riboflavin), a dihydropyridine (e.g. nifedipine), folic acid or analogues. After polymerisation the polymer is freed from the template by a washing procedure. The template can also come from the group of dioxins (e.g. tetrachlorodioxodibenzene, TCDB), polyaromatic hydrocarbons (PAHs), aldehydes, ketones, halogenated hydrocarbons and phosphonates (e.g. nerve agents like sarin, soman, tabun, VX). This procedure results in a polymer showing unprecedentedly high selectivity and strong binding of the template or structurally related compounds.

Example 26

The polymer prepared according to Example 11 can be used for separation of enantiomers, diastereomers of the template or for separation of the template or template analogues from structurally related compounds present in a complex mixture. This can be done by chromatography, capillary electrophoresis, capillary electrochromatography, batch modes or membrane modes. The polymer can further be used for catalysing chemical reactions such as esterolysis, amidolysis, ester synthesis or amide synthesis.

LITERATURE

1. R. A. Bartsch, M. Maeda, Eds., *Molecular and Ionic Recognition with Imprinted Polymers* (Oxford University Press, Washington, 1998).
2. L. I. Andersson, R. Müller, G. Vlatakis, K. Mosbach, Mimics of the binding sites of opioid receptors obtained by, *Proc. Natl. Acad. Sci. U.S.A.* 92, 4788-92 (1995).
3. B. Sellergren, Polymer- and template-related factors influencing the efficiency in molecularly imprinted solid-phase extractions, *Trends Anal. Chem.* 18, 164-174 (1999).
4. B. Sellergren, M. Lepistoe, K. Mosbach, Highly enantioselective and substrate-selective polymers obtained by interactions. NMR and chromatographic studies on the nature of recognition, *J. Am. Chem. Soc.* 110, 5853-60 (1988).
5. B. Sellergren, in *A practical approach to chiral separation by liquid chromatography* G. Subramanian, Ed. (VCH, Weinheim, 1994) pp. 69-93.
6. K. J. Shea, D. A. Spivak, B. Sellergren, Polymeric complements for adenine prepared by molecular imprinting, *J. Am. Chem. Soc.* 115, 3368-3369 (1993).
7. B. Sellergren, Direct drug determination by selective sample enrichment on an imprinted polymer, *Anal. Chem.* 66, 1578 (1994).

8. E. Fan, S. A. Van Arman, S. Kincaid, A. D. Hamilton, Molecular recognition: Hydrogen bonding receptors that function in highly competitive solvents, *J. Am. Chem. Soc.* 115, 369-370 (1993).
9. Lieser, Kemmner, *Chem. Ber.* 84, 4-12 (1951).
10. Iwakura et. al. Jpn., 186-191 (1968), *Bull. Chem. Soc.* 41, 186-191 (1968).
11. e. a. Seiller, *Tetrahedron* 51, 10901-10912 (1995).
12. Oikawa, *J. Polym. Sci.: Part A: Polym. Chem.* 31, 457-465 (1993).
13. D. Spivak, K. J. Shea, Molecular Imprinting of Carboxylic Acids Employing Novel Functional Macroporous Polymers, *J. Org. Chem.* 64, 4627-4634 (1999).
14. M. J. Kamlet, R. M. Doherty, J.-L. M. Abboud, M. H. Abraham, R. W. Taft, Solubility. A new look., *Chemtech*, 566-576 (1986).
15. M. C. Etter, T. W. Panunto, 1,3-Bis(m-nitrophenyl)urea: An exceptionally good complexing agent for proton acceptors., *J. Am. Chem. Soc.* 110, 5896-5897 (1988).
16. G. Wulff, R. Schönfelt, Polymerizablöe amidines—Adhesion mediators and binding sites for molecular imprinting, Adv. Mater. 10, 957-959 (1998).
17. C. Dauwe, J. Buddrus, GIT-Fachzeitschrift für das Laboratorium 38, 517 (1994).
18. Fuks, Tetrahedron 29, 2147-2151 (1973).
19. E. J. Roskamp, S. F. Pedersen, J. Am. Chem. Soc. 1957, 109, 3152-3154.

The invention claimed is:

1. A molecularly imprinted polymer obtained by polymerization of at least one polymerizable formamidine monomer in the presence of a template molecule, and extraction of the template molecule after the polymerization.

2. A molecularly imprinted polymer according to claim 1, comprising a crosslinking monomer.

3. A molecularly imprinted polymer according to claim 2, wherein the template monomer is selected from the group consisting of a nucleotide or oligonucleotide, a polyelectrolyte such as polysulfonic or polycarboxylic or mixed polysulfonic/polycarboxylonic acid, a protein, a peptide, an amino acid, a carboxylic acid, a phosphonic acid, a phosboric acid or phosphinic acid, a sulfuric, sulfonic, sulfinic acid, an alcohol, an imide, a thiol, a ketone, an amide, a sulfonamide, a phosphonamide, a hydantoin, a barbiturate, an ether, a polyaromatic hydrocarbon, a phosphonate, and an aldehyde.

4. A process for separating enantiomers and/or diastereomers of said template molecule from structurally related compounds, utilizing the polymer according to claim 2.

5. A process for separating enantiomers and/or diastereomers of said template molecule from structurally related compounds, utilizing the polymeer according to claim 3.

6. A process for separating a template molecule or analogues thereof from structurally related compounds, utilizing the polymer according to claim 2.

7. A process for separating a template molecule or analogues thereof from structurally related compounds, utilizing the polymer according to claim 3.

* * * * *